United States Patent [19]

Baier et al.

[11] Patent Number: 4,966,578

[45] Date of Patent: Oct. 30, 1990

[54] APPARATUS FOR THE INSUFFLATION OF GAS INTO A BODY CAVITY

[75] Inventors: Manfred Baier; Roland Schäfer, both of Bretten-Diedelsheim, Fed. Rep. of Germany

[73] Assignee: Richard Wolf GmbH, Fed. Rep. of Germany

[21] Appl. No.: 201,936

[22] Filed: Jun. 3, 1988

[30] Foreign Application Priority Data

Jun. 4, 1987 [DE] Fed. Rep. of Germany ....... 3718717

[51] Int. Cl.$^5$ ........................................... A61M 37/00
[52] U.S. Cl. ...................................... 604/26; 128/748
[58] Field of Search ................................ 604/23, 26; 128/747–748, DIG. 12, DIG. 13

[56] References Cited

U.S. PATENT DOCUMENTS

| | | | |
|---|---|---|---|
| 3,858,572 | 1/1975 | Binard et al. | 604/26 X |
| 4,464,169 | 8/1984 | Semm | 604/26 |
| 4,676,774 | 6/1987 | Semm et al. | 128/748 X |

FOREIGN PATENT DOCUMENTS 3000218  6/1983  Fed. Rep. of Germany.

Primary Examiner—Max Hindenburg
Assistant Examiner—John P. Lacyk
Attorney, Agent, or Firm—Hill, VanSanten, Steadman & Simpson

[57] ABSTRACT

In an apparatus for the insufflation of gas into a body cavity the dynamic pressure of the gas flow conducted to the body cavity and the static intra-abdominal pressure in the body cavity are detected with at least one measuring transducer. The electrical output signal of the measuring transducer detecting the pressure is converted by difference formation with a compensation signal, which substantially takes into account the resistance to flow of the instrument conducting the gas into the body cavity, into a difference signal corresponding to the static intra-abdominal pressure. With this signal a control circuit for the setting of the desired pressure value in the body cavity is controlled, in which respect the compensation signal in each case at the start of the insufflation is generated from the output signal of the relevant measuring transducer and is stored in a store and upon gas flow the stored compensation signal is fed to the one input and the output signal of the measuring transducer is fed to the other input of an operational amplifier for the formation of the difference signal, whilst the store at the input store is separated electrically from the measuring transducer by way of a switch.

9 Claims, 2 Drawing Sheets

APPARATUS FOR THE INSUFFLATION OF GAS INTO A BODY CAVITY

BACKGROUND OF THE INVENTION (a) Field of the Invention

This invention relates to an apparatus for the insufflation of gas into a body cavity, more particularly, of the kind in which the dynamic pressure of the gas flow conducted to the body cavity and the static intra-abdominal pressure in the body cavity are detected with at least one measuring transducer of which the electrical output signal for detecting the pressure is converted by difference formation with a compensation signal, which substantially takes into account the resistance to flow of an instrument for conducting the gas into the body cavity, into a difference signal which corresponds to the static intra-abdominal pressure and with this signal a control circuit for the adjustment of the desired pressure value in the body cavity is controlled.

(b) Description of the Prior Art

A special problem with the insufflation of gas into a body cavity, for example during a surgical operation, consists in generating with the gas flow a constant intra-abdominal pressure within physiologically acceptable limits and in measuring this pressure accurately. In the case of modern apparatus of the aforementioned kind, the supply of the gas into the body cavity and the measurement of the static intra-abdominal pressure is effected utilizing a single tube or pipe. Thus, for example, DE-PS No. 30 00 218 discloses an insufflation apparatus in which, in an internal operation, gas is insufflated through a supply pipe, after that the gas flow is switched off and then the pressure through the same pipe is measured. This method involving intermittent gas inflow and pressure measurement by way of a supply pipe leads perforce to a regular interruption of the gas flow and can lead to exceeding the desired value, to be preselected, of the intra-abdominal pressure, namely when a gas flow phase starts just before the desired pressure value is reached.

Equally, in the device disclosed in EP-OS No. 0 169 972, merely one pipe is provided for the gas flow and the pressure measurement. In this specification it is proposed, after a single compensation, undertaken at the start of the entire insufflation procedure, of the system resistance, which is dictated mainly by the instrument projecting into the body cavity, for example a Veress needle, constantly to ascertain the static intra-abdominal pressure by the substraction of the system resistance pressure from the total pressure and to indicate same to the doctor. This proposal has however, the disadvantage that a change in resistance, caused for example by a change of instrument, a retrocession of the flow as a result of low pressure difference between inlet and outlet or by kinking of the hose is not taken into account during the continuance of the insufflation procedure.

SUMMARY OF THE INVENTION

Accordingly, the main object of the present invention is to provide an apparatus for the insufflation of gas into a body cavity in which there is constant measuring of the intra-abdominal pressure and monitoring of possible variations in the pressure system up and measuring throughout the entire insufflation procedure.

To this end, and from one aspect, the present invention consists in apparatus for the insufflation of gas into a body cavity, in which the dynamic pressure of the gas flow conducted to the body cavity and the static intra-abdominal pressure in the body cavity are detected with at least one measuring transducer of which an electrical output signal of a measuring transducer for detecting the pressure is converted by difference formation with a compensation signal, which substantially taken into account the resistance to flow of an instrument for conducting the gas into the body cavity, into a difference signal which corresponds to the static intra-abdominal pressure and with this signal a control circuit for the adjustment of the desired pressure value in the body cavity is controlled, characterised in that the compensation signal in each case, at the start of the insufflation, is generated from the output signal of the relevant measuring transducer and is stored in a first store and in that upon gas flows, the stored compensation signal is fed to the one input and the output signal of the measuring transducer is fed to the other input of a first operation amplifier for the formation of the difference signal, whilst the store at the input side is electrically separated from the measuring transducer by way of a first switch.

In accordance with this aspect of the invention compensation of the system resistance by means of an electronics system which can recognise variations in the pipe system is initiated also at the points in time at which these variations take place. In this respect, the invention has the advantage that, upon operation of an insufflation apparatus, there are various points in time at which the apparatus is brought from the flow "off" state into the "on" state, for example upon the switching-on of the apparatus, upon the keeping constant of the desired pressure in the body cavity, which takes place through short insufflation surges, or upon variations of the resistance to flow as a result of instrument change or flow fluctuations. At these points in time, counter-connected to the measuring circuit is a compensation signal which has previously been ascertained in a compensation circuit and which takes into account substantially the resistance to flow of the instrument conducting the gas into the body cavity immediately prior to the change from the "off" state into the flow "on" state. This compensation signal remains counter-connected to the measuring circuit during the entire flow "on" phase.

Accordingly, by means of the invention the result is achieved that at all times the actual internal pressure in the body cavity can be brought to the knowledge of the operating personnel on a display and this pressure is decisive for regulating the apparatus to a desired pressure.

Preferably, the store is a capacitor which is connected by way of an impedance transformer having high input resistance and low output resistance to the said one input of the first operational amplifier.

In a preferred embodiment of the invention, the output signal which corresponds to the desired intra-abdominal pressure and which is generated by the measuring transducer is, with the gas flow shut off, stored by way of a closed second switch in a second store and is conducted to the one input of a second operational amplifier. With the switching-on of the gas flow, the second switch opens for a short time and the dynamic output signal of the measuring transducer is imparted to the other input of the second operational amplifier which from the two input signals by difference formation generates the compensation signal which is then stored in the first store.

Advantageously, the first store, upon each switching-on of the gas flow, is cleared and is then loaded with the compensation signal actualized in view of the desired pressure value.

From another aspect, the present invention consists in apparatus for the insufflation of gas into a body cavity, in which the flow of the gas conducted to the body cavity is detected with a measuring transducer which can be compensated to a zero position and with the resulting output signal of the measuring tranducer a control circuit is controlled in order to regulate the gas flow to a desired value with an adjusting member located in the gas pipe, characterised in that a no-load signal which occurs when the measuring transducer is unloaded at the input side is fed to the one input of an operational amplifier which forms a difference signal from the amounts of this no-load signal and of a compensation signal fed to its other input, in that the output signal of the said one operational amplifier is amplified with a further operational amplifier and, with the output signal thereof by way of a time member, an electrical store (C3) is loaded which communicates permanently with the said other input of the one operational amplifier and in that the store is separable from the output of this operational amplifier by opening of a contact.

Thus in accordance with this aspect of the invention, that part which regulates the amount of gas flow to the instrument conducting the gas into the body cavity, i.e. the flow regulating circuit, is advantageously so designed that tendencies of measuring transducers, which are used to convert a pressure into an electrical signal, to vary their output value upon non-loading by temperature changes within the apparatus as a result of the development of heat or also ageing are compensated for by a constant zero-point equalisation. For this, a special compensation circuit is provided in the flow regulating circuit, which has the advantage that the gas flow can at all times be regulated exactly and irrespectively of the thermal offset characteristic or ageing -dictated variations of the measuring transducer.

Preferably, the time member is an RC-member having a capacitor which serves as a store.

In a preferred embodiment, the contact is connected into the connection between the said further operational amplifier and the store.

BRIEF DESCRIPTION OF THE DRAWINGS

In order that the invention may be more readily understood some embodiments thereof will now be described, by way of example, with reference to the accompanying drawings, in which.

DESCRIPTION OF THE PREFERRED EMBODIMENTS

Figure 1:
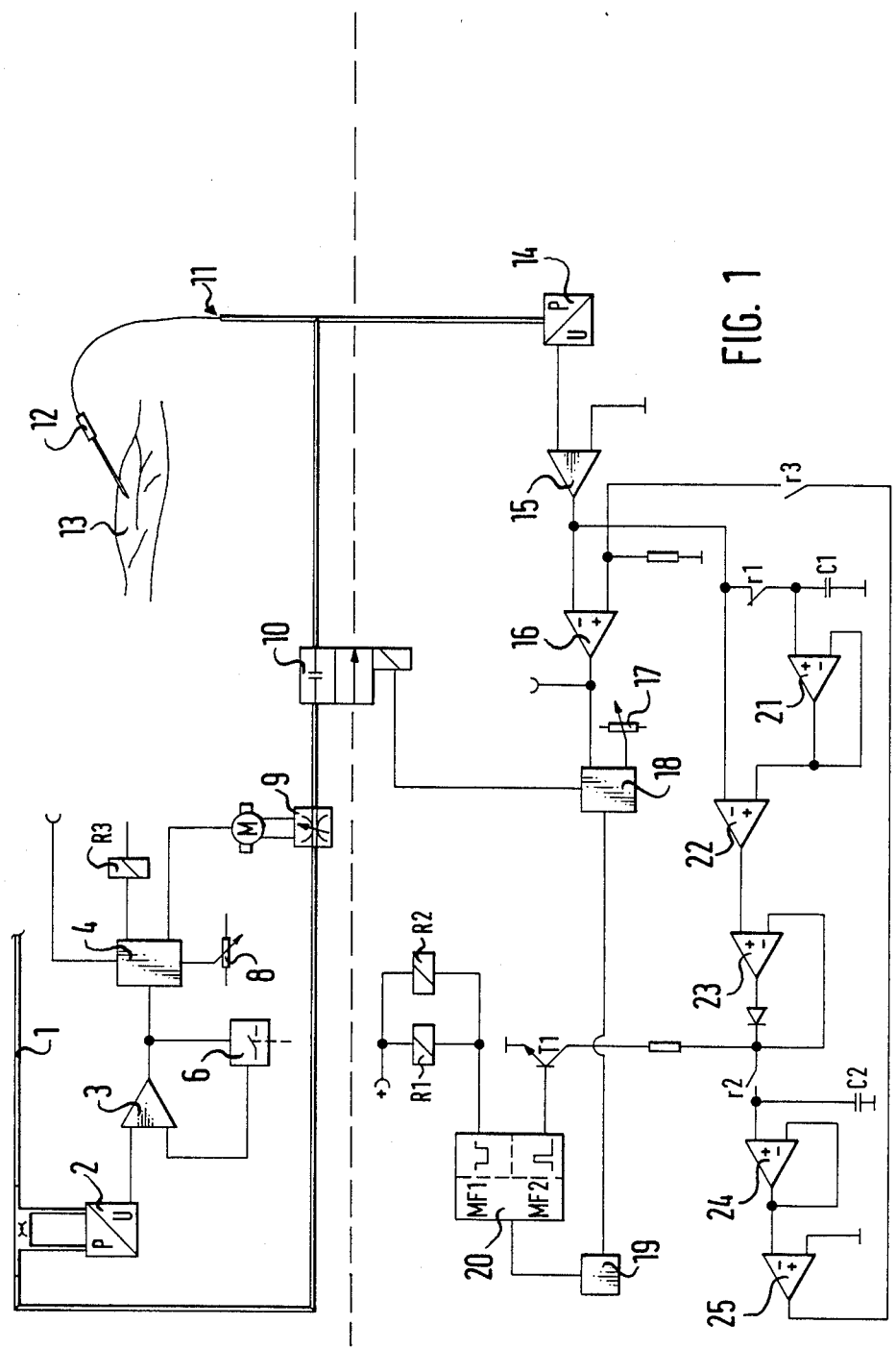
FIG. 1 shows a diagrammatic circuit arrangement of an apparatus for the insufflation of gas into a body cavity and constructed in accordance with the invention with the upper part of the drawing showing a flow regulating circuit and the lower part of the drawings showing a pressure regulating circuit.

Referring to FIG. 1 of the drawings, gas is conducted out of a pressure container (not shown) by way of a gas inlet into the gas pipe 1 of the apparatus. After passage through a flow regulating circuit of the insufflator, the gas passes out of a gas outlet 11 and through an instrument 12 for example a Veress needle which conducts the gas into a body cavity 13.

The flow regulating circuit comprises a differential-pressure measuring transducer 2 which is connected to the gas pipe 1 and the output signal of which is conducted to an input of an operational amplifier (OP) 3. The output signal of the amplifier 3 is fed as actual-value signal to an electronic regulator 4 which compares the actual-value signal with a desired-value signal preselected by an adjuster 8. Upon deviation of the actual value from the desired value of the gas flow, the electronic regulator 4 is operative by means of an analog adjusting member 9 to bring the gas flow back to the desired value. This can be achieved by means of a throttle which is acted upon by the adjusting member 9 to narrow or widen the passage of the gas flow 1. The now constant gas flow passes through a valve 10 to the gas outlet 11. Between the output of the amplifier (OP) 3 and its second input a compensation circuit 6, to be more fully described, may be provided, which ensures zero-point equalisation of the amplifier (OP) 3 when the measuring transducer 2 is not loaded.

The pressure prevailing at the outlet end of the gas pipe 1 is detected in the pressure regulating circuit by a pressure measuring transducer 14 which converts the detected pressure into a corresponding electrical signal. An operational amplifier (OP) 15 connected subsequently to the measuring transducer 14 conducts the measuring signal to the one input of an operational amplifier (OP) 16, the output of which is connected to a pressure display or indicator (not shown) and to an electronic evaluator 18. This electronic evaluator 18 compares the instantaneous actual-value signal at the output of the (OP) 16 with a desired-value signal which is to be selected by means of an adjuster 17. Electronic evaluator 18 is connected to the valve 10 which is controlled, as a function of the result of the comparison between the desired-and actual-value signal in the electronic evaluator 18, in such a way that the gas flow in the gas pipe 1 is switched when the desired pressure is reached in the body cavity, that is to say upon equality between the actual-value-signal and the desired-value-signal in the electronic evaluator 18.

In operation the apparatus changes over at various points in time from the flow "off" state into the flow "on" state, for instance upon the switching-on, upon keeping-constant of the desired pressure in the body cavity 13, which takes place through short insufflation surges, or upon variations of the resistance to flow of the pressure system as a result of a change of the instrument 12 or flow fluctuations.

An electronic control 19 coupled to the electronic evaluator 18 recognises and controls these "off"-"on" states. Two monostable flip flops MF1 and MF2 are connected subsequently to it at 20. Upon the change-over from the flow "off" state of the apparatus into the flow "on" state, in the electronic control 19, a rising pulse edge is generated, which for its part triggers the subsequently-connected monostable flip flops MF1 and MF2. Connected subsequently to the flip flop MF1 are two relays R1 and R2, which are activated for the duration of the pulse on the flip flop MF1. The relays R1 and R2 open or close respectively two switches r1 or r2 respectively in a compensation circuit, to be hereinafter described. The pulse which is generated by MF2 and the pulse duration of which is considerably shorter than that of the pulse in MF1, drives or switches a subsequently-connected transistor T1, the function of which will be hereinafter described.

The output signal of the (OP) 15 is fed, besides to the direct feed wire to the (OP) 16, at the same time to the said compensation circuit. On the one hand it is conducted directly onto one input of an operational amplified (OP) 22, on the other hand it is switchable by way of a switch r1, controlled by the relay R1, onto an operational amplifier (OP) 21 connected to an impedance transformer and having high input resistance and slight output resistance and also a capacitor C1 connected between the input of the (OP) 21 and earth. The output of the (OP) 21 is connected to the second input of the (OP) 22. (OP) 22 amplifies the voltage difference, the peak value of which is obtained by way of the subsequently connected operational amplifier (OP) 23 with diode at the output thereof. The output of the (OP) 23 with diode is on the one hand connected to the said transistor T1, on the other hand it is switchable by way of a switch r2, controlled by the relay R2, onto an operational amplifier (OP) 24 connected as an impedance transformer as well as onto a capacitor C2 connected between the input of the (OP) 24 and earth. The output of the (OP) 24 is amplified in the subsequently connected operational amplifier (OP) 25 and is conducted by way of a switch r3, which is opened in the flow "off" state of the apparatus and is closed in the flow "on" state, onto the other input of the (OP) 16.

In detail the pressure measurement with the described circuit arrangement functions as follows.

If the gas flow is switched off, then in the outlet end of the gas pipe 1 the static intra-abdominal pressure obtains, which is totally unaffected by a flow pressure. This value is brought in the form of a corresponding voltage by way of (OP) 15 and (OP) 16 to the pressure display or indicator and at the same time onto the compensation circuit, in which respect the value is conducted by way of the switch r1, closed in this operating state, onto the capacitor C1 and is stored there. The value is conducted by way of (OP) 21 onto the input of the (OP) 22, the second input of which is connected directly to the measuring voltage. Since at the input side at the (OP) 22 both values are the same, no further signal processing is effected in this phase.

If now the gas flow is switched on again, for instance if the actual value of the static intra-abdominal pressure is less than the desired value, the switches r1 and r2 are, in this switch-on phase, opened or respectively closed briefly by the relays R1 and R2 controlled by the flip flop MF1. At the same time, through the pulse, generated by the flip flop MF2, by way of T1 and the now closed switch r2 the capacitor C2 is short-circuited, so that a voltage value stored in C2 upon a previous switching-on of the gas flow is cleared. With the switching-on, the switch r3 is closed. In this phase there obtains at the measuring transducer 14 the static intra-abdominal pressure as well as the dynamic pressure of the gas flow, the value of which it is essential to compensate for. The voltage value, increased by reason of the increased pressure value, at (OP) 16 is conducted to (OP) 22. Since, in this phase, the switch r1 is opened, the voltage previously obtaining at C1, which was applied upon flow "off" state and represents the value of the static intra-abdomindal pressure, is conducted by way of (OP) 21 furthermore onto the second input of (OP) 22. Accordingly, the voltage at the output of the (OP) 22 represents only the dynamic part of the overall pressure present at the transducer and thus the insufflation pressure. The peak value of the output voltage of the (OP) 22 is obtained by way of (OP) 23 and diode. With this peak value the capacitor C 2 is charged by way of the switch r2 closed in this phase. It is conducted by way of (OP) 24 and (OP) 25 and closed switch r3 as offset onto the second input of the (OP) 16, at the output of which now merely the voltage value representing the static part of the total pressure appears and is displayed.

The duration of this transition phase lies in the millisecond region. After that the relays R1 and R2 are again inactive, that is to say switch r1 is again closed and switch r2 again opened. The voltage value stored at the capacitor C2 is conducted furthermore up till the end of the insufflation phase as offset onto (OP) 16. The value corresponds exactly to the superelevation which the connected instrument 12 causes. Measured values which now lie amountwise higher than this value can be caused only by an external pressure. Here this is the intra-abdominal pressure in the body cavity 13 and thus the pressure which is decisive for the regulation of the apparatus to the set desired pressure.

An advantageous further development of the flow regulation consists, as mentioned above, in the incorporation of a compensation circuit 6. This compensation circuit serves for the zero balancing of the measuring transducer 2 in the unloaded state.

If the measuring transducer 2 is unloaded, in the normal case a voltage of zero volts should occur at its output. This can, however, be different by reason of temperature changes within the apparatus as a result of the development of heat or also caused by ageing.

Figure 2:
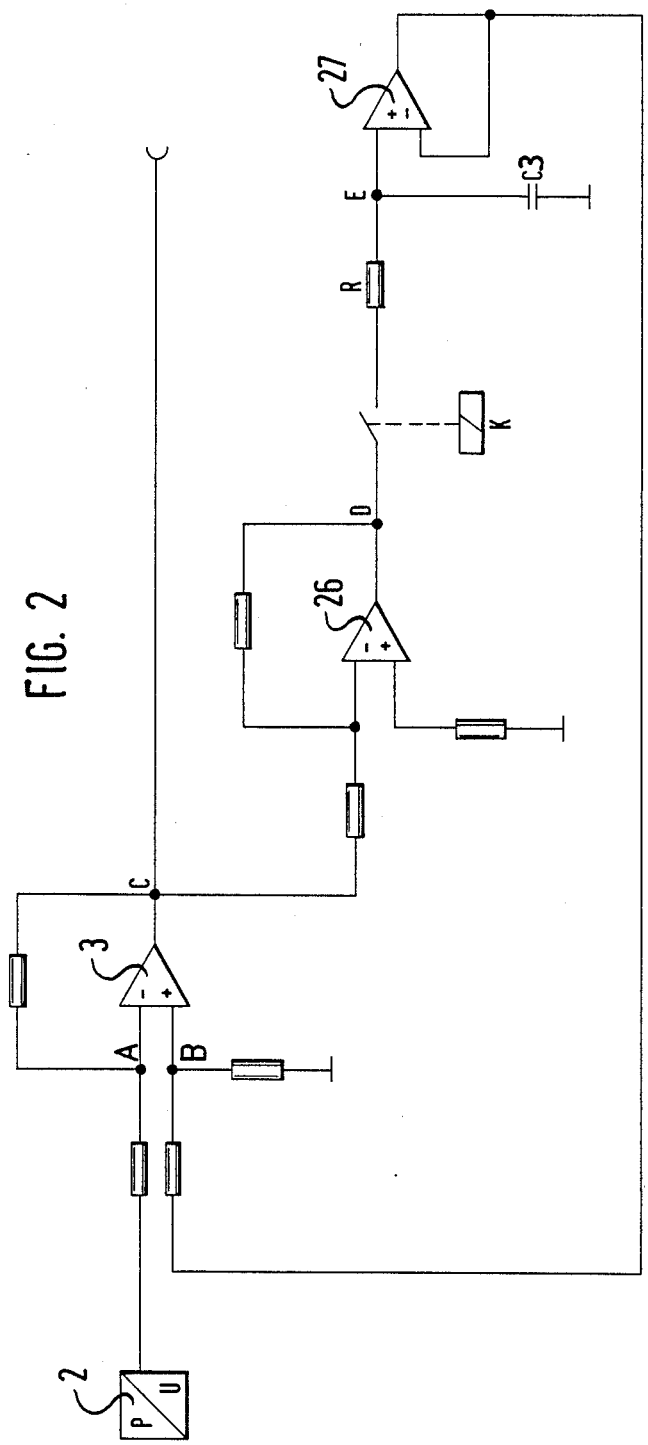
FIG. 2 shows a compensation circuit for the zero-point equalisation of a pressure measuring transducer, as is used in accordance with an advantageous further development in the flow regulating circuit of FIG. 1.

In the circuit in accordance with FIG. 2, a voltage generated by a measuring transformer 2 is conducted onto one input of operational amplifier (OP) 3. The output of (OP) 3 is conducted onto an amplifier circuit with operational amplifier (OP) 26, which has a high amplification. The output signal of (OP) 26 is switchable by way of a contact K, which is always closed whenever the measuring transducer 2 is unloaded, by way of a time member RC onto an electrical store (in FIG. 2) (C3). In the further course, the signal is returned by way of an operational amplifier (OP) 27, which is connected as an impedance transformer, to the second input of the (OP) 3.

The compensation is activated with the closing of the contact, thus always when the measuring transducer 2 is unloaded. This is the case when the set desired value of the intra-abdominal pressure is reached and the gas flow is switched off, since there is this case also no longer a pressure drop, and the same upon the switching-on of the apparatus.

The mode of operation of the circuit is made clear with the aid of an example.

Let us assume that the measuring transducer 2 is unloaded and the contact accordingly closed. At the output of the measuring transducer 2 there stands a voltage of +1 volt, at the point B a voltage of :0.2 volt. Let us assume that the amplification factor of (OP) 3 amounts to 1, and that of (OP) 26 amounts to 1000.

Under these assumptions, point A is thus by 0.8 volt more positive than point B. Accordingly, point C at the output of the (OP) 3 lies amountwise likewise at 0.8 volt, circuit-occasioned by with negative sign, thus minus 0.8 volt. Since (OP) 26 has a high amplification, this would travel into the saturation to about 11 volt with positive sign on account of the inverting behaviour of (OP) 26. The capacitor C3 is charged by way of the resistor R with the value standing at the point D, in which respect the RC-member brings about a slower rise of the voltage at the points E and B than at the point D. The same voltage is conducted by way of (OP) 27 without signa reversal to the point B. If the voltage at the points D, E and B has reached the value, to be compensated, of +1 volt at the point A, (OP) 26 ceases running into the saturation of +11 volt.

Since then the voltage values at the points A and B are the same, point C lies at nil volt. Since (OP) 26 now does not have to amplify a voltage, point D likewise lies at nil. At the capacitor C3 there now lies a voltage of +1 volt, so that it could discharge itself again by way of the (OP) 26. However, this is compensated for by the closed control loop, as described.

If now the contact K opens, there obtains furthermore at the capacitor C3 the voltage of +1 volt, which is needed in order to level control, stabilize or bring the point C to zero volt. If now there occurs at the point A as a result of a pressure drop at the measuring transducer 2 a voltage differing from +1 volt, this is considered as the measuring voltage and further processed.

The open control or regulating circuit prevents a further compensation. The previously obtained compensation voltage at the capacitor C3 is maintained, depending on the dimensioning of R, C3 and (OP) 27, for 5 up to 60 min. at the point B. The described regulating procedure takes its course in the region of milliseconds.

The circuit can also be used to generate a virtual nil point. For example, a specific pressure can be imparted to the measuring transducer 2 and the voltage value, resulting therefrom, at the point A can be compensated by brief closure of the contact K and be considered as zero point. Only pressures deviating from this specific pressure would then have to be evaluated.

It should be appreciated that the invention is not limited to the embodiments herein described but includes all modifications and variations falling within its scope.

What is claimed is:

1. An apparatus for the insufflation of gas into a body cavity, said apparatus including means for detecting a dynamic pressure of the gas flow conducted tot he body cavity and a static intra-abdominal pressure in the body cavity, said means including measuring transducer means for producing an electrical output signal, means for converting the electrical output signal by a difference formation with a compensation signal, which substantially takes into account the resistance to flow of an instrument for conducting the gas into the body cavity, into a difference signal which corresponds to the static intra-abdominal pressure, and control circuit means for the adjusting of the desired pressure value in the body cavity in response to said difference signal, the improvements comprising first means for generating the compensation signal in each case at the start of the insufflation from the output signal of the measuring transducer means and storing the compensation signal in a first store, a first switch interposed between said first store and said transducer means, and when gas flows said first means feeding the stored compensation signal to one input of a first operational amplifier and as the output signal of the measuring transducer means is being fed to the other input of the first operational amplifier for the formation of the difference signal, whilst said first switch is opened to electrically separate an input side of the first store from the measuring transducer means.

2. Apparatus according to claim 1 wherein said first store is a capacitor which is connected by way of an impedance transformer having high input resistance and low output resistance to said input of the said first operational amplifier.

3. Apparatus according to claim 10, characterised in that the output signal which corresponds to the desired intra-abdominal pressure and which is generated by the measuring transducer means is, with the gas flow shut off, stored by way of a closed second switch in a second store and is conducted to the one input of a second operational amplifier, in that with the switching-on of the gas flow the second switch opens for a short time and the dynamic output signal of the measuring transducer means is fed to the other input of the second operational amplifier which from the two input signals by difference formation generates the compensation signal, and in that the compensation signal is stored in the first store.

4. Apparatus according to claim 10, wherein in that the first store upon each switching-on of the gas flow is cleared and is then loaded with the compensation signal actualised in view of the desired pressure value.

5. An apparatus according to claim 1, wherein the control circuit means includes an adjustment member located in a gas pipe, said apparatus including second measuring transducer means for detecting the gas flow being conducted to the body cavity producing an output signal applied to the control means, said second measuring transducer means being compensated to a zero position including a second operational amplifier having an input connected to the second measuring transducer means, an output being connected to a third operational amplifier having an output being connected through a second switch to a time member and an electrical store, said electrical store being in permanent contact with a second input of the second amplifier, the second switch electrically separating said second store from the third operational amplifier so that when the second measuring transducer means is unloaded, it produces a no-load signal applied to the second operational amplifier which receives a compensation signal from said second store to produce a different signal which is then applied to the third operational amplifier.

6. An apparatus for the insufflation of gas into a body cavity, said apparatus having control circuit means for regulating a gas flow to a value in a gas pipe including an adjustment member located in the pipe, and measuring transducer means for detecting the gas flow being conducted to the body cavity, said transducer means being compensated to zero position and producing a resulting output signal for said control circuit means, the improvements comprising a first operational amplifier having an input connected to the output of the measuring transducer means, a second input and an output, said output being connected to a second operational amplifier having an output connected through a switch to time member connected to an electrical store, said store being permanently connected to the second input of the first operational amplifier so that the output of the store compensates a no-load signal that occurs when the measuring transfer means is unloaded.

7. Apparatus according to claim 6, characterised in that the time member is an RC-member, the capacitor of which serves as a store.

8. Apparatus according to claim 6, characterised in that the switch is connected into the connection between the second operational amplifier and the store.

9. Apparatus according to claim 7, characterised in that the switch is connected into the connection between the second operation amplifier.

* * * * *